(12) United States Patent
Matthew et al.

(10) Patent No.: US 10,729,610 B2
(45) Date of Patent: Aug. 4, 2020

(54) SEMI-PASSIVE CONTROL SYSTEM AND METHOD FOR ASSISTIVE ORTHOSES

(71) Applicant: THE REGENTS OF THE UNIVERSITY OF CALIFORNIA, Oakland, FL (US)

(72) Inventors: Robert Peter Matthew, Berkeley, CA (US); Eric John Mica, Daly City, CA (US); Waiman Meinhold, Santa Barbara, CA (US); Joel Alfredo Loeza, Bakersfield, CA (US); Ruzena Bajcsy, Kensington, CA (US); Masayoshi Tomizuka, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 231 days.

(21) Appl. No.: 15/551,699

(22) PCT Filed: Feb. 18, 2016

(86) PCT No.: PCT/US2016/018394
§ 371 (c)(1),
(2) Date: Aug. 17, 2017

(87) PCT Pub. No.: WO2016/134103
PCT Pub. Date: Aug. 25, 2016

(65) Prior Publication Data
US 2018/0036194 A1    Feb. 8, 2018

Related U.S. Application Data

(60) Provisional application No. 62/117,534, filed on Feb. 18, 2015.

(51) Int. Cl.
*A61H 1/00* (2006.01)
*A61H 3/00* (2006.01)
(Continued)

(52) U.S. Cl.
CPC ............... *A61H 1/00* (2013.01); *A61F 5/01* (2013.01); *A61H 3/00* (2013.01); *B25J 9/0006* (2013.01); *B25J 9/104* (2013.01); *B25J 9/14* (2013.01)

(58) Field of Classification Search
CPC ...... A61F 2/64; A61F 2/68; A61F 2/70; A61F 2/72; A61F 2/74; A61F 2/76; A61F 5/00;
(Continued)

(56) References Cited

U.S. PATENT DOCUMENTS

| 5,662,693 A | 9/1997 | Johnson et al. |
| 6,821,259 B2 | 11/2004 | Rahman et al. |

(Continued)

FOREIGN PATENT DOCUMENTS

WO    2014109799 A1    7/2014

*Primary Examiner* — Marcia L Watkins
(74) *Attorney, Agent, or Firm* — Jorie L. Stroup; Roberts Calderon Safran & Cole P.C.

(57) ABSTRACT

Semi-passive control system (10) comprises a pneumatic spring actuator (16), a pressure regulator (22) in communication with the pneumatic spring actuator (16), a hydraulic locking actuator (18), a hydraulic valve (20) in communication with actuator (18), a power source (14), a pulley wheel (42), and a cable (46) having a first end in contact with pulley wheel (42), first and second side portions (50, 56) extending from opposing sides of pulley wheel (42), and a second end adapted to connect to an orthosis device (76). At least one cable clamp (62) attaches to second side portion (56) of cable (46) and interconnects cable (46) to shafts (112b, 118b) of actuators (16, 18). A central control unit (12) includes a processor (13a) and a computer readable storage medium (13b) having program instructions stored thereon for execution by the central control unit to adjust stiffness, damping or stiffness and damping parameters.

14 Claims, 8 Drawing Sheets

(51) Int. Cl.
*B25J 9/00* (2006.01)
*B25J 9/10* (2006.01)
*B25J 9/14* (2006.01)
*A61F 5/01* (2006.01)

(58) Field of Classification Search
CPC .. A61F 5/01; A61F 5/052; A61H 3/00; A61H 1/00; B25J 9/0006
USPC ............ 600/595; 601/5, 34, 35; 602/16, 26; 623/24–27, 56–65
See application file for complete search history.

(56) References Cited

U.S. PATENT DOCUMENTS

| | | |
|---|---|---|
| 7,396,337 B2 | 7/2008 | McBean et al. |
| 8,409,117 B2 | 4/2013 | Cheng et al. |
| 8,585,620 B2 | 11/2013 | McBean et al. |
| 8,834,169 B2 | 9/2014 | Reinkensmeyer et al. |
| 2009/0264799 A1 | 10/2009 | Bonutti et al. |
| 2013/0261766 A1 | 10/2013 | Langlois et al. |
| 2014/0358053 A1 | 12/2014 | Triolo et al. |

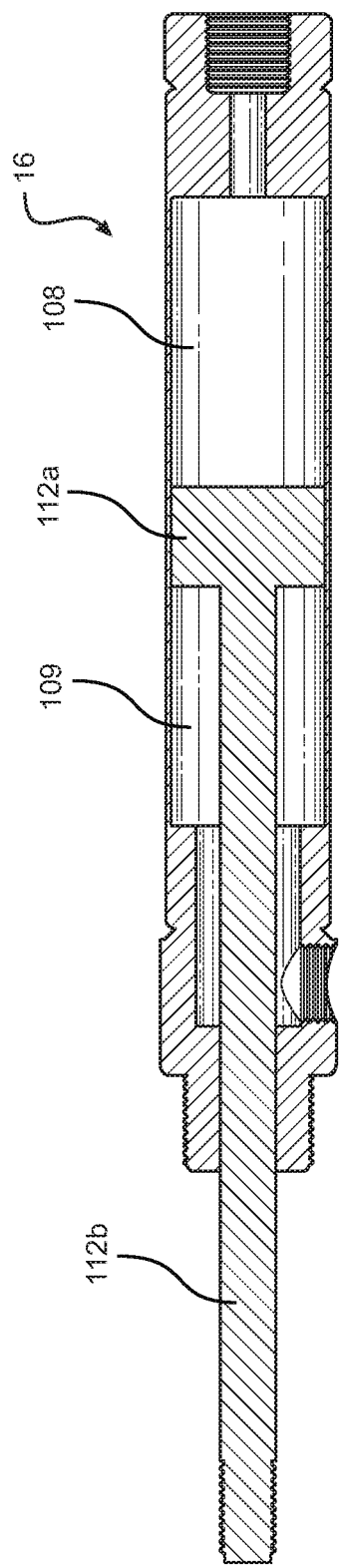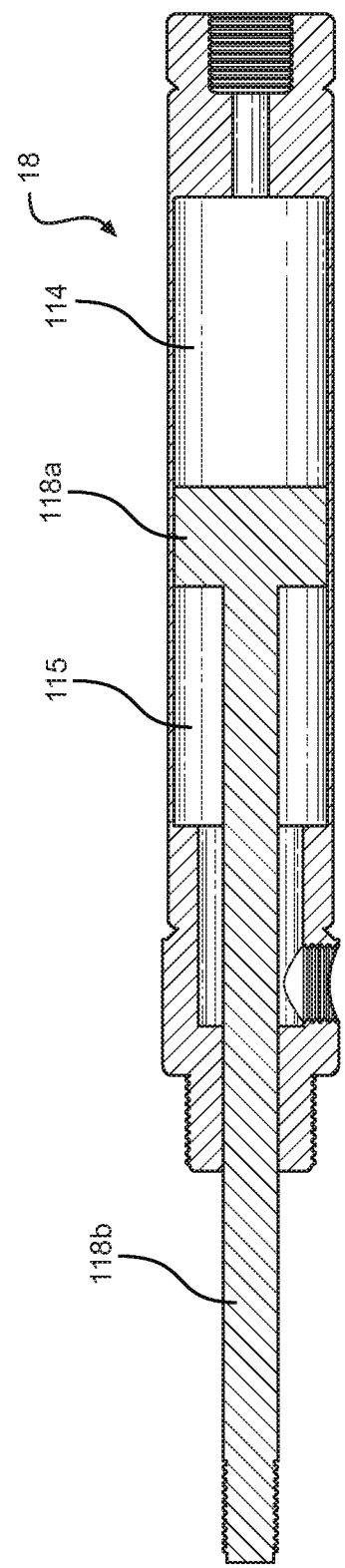
FIG. 5
FIG. 6

SEMI-PASSIVE CONTROL SYSTEM AND METHOD FOR ASSISTIVE ORTHOSES

This invention was made with United States Government support under grant Nos. 1354321 and 1362172 awarded by the National Science Foundation (NSF). The U.S. Government has certain rights in the invention.

BACKGROUND

1. Field of the Invention

The present invention pertains to the art of orthosis devices, and more particularly, to assistive orthosis devices for upper limbs.

2. Discussion of the Prior Art

Existing assistive orthosis devices either use active or passive methods to assist an individual. Active devices use direct current (DC) motors to provide assistive torque to limbs of an individual. To change the perceived damping and stiffness felt by the wearer of an orthosis device, controllers need to be implemented. This requires the motors to be constantly run, which consumes a lot of power. The controllers are also complicated, making the modeling of a user very important and the motors expensive and specialized. Passive devices can provide assistance through fixed springs and dampers, which do not require electricity to operate. However the parameters (e.g. settings) of the fixed springs and dampers may not be suitable for every task. For instance, if a device holds the arm in front of the user, they will have difficulties holding their arm above their head, or down by their side.

U.S. Pat. No. 6,821,259 depicts an orthosis device including two limb sections pivotally attached to each other. Each limb section includes a four-bar linkage and a spring member adapted to provide an equilibrium-inducing force, allowing a user with muscular abnormalities to move his or her limb and hold them in place. U.S. Pat. No. 8,834,169 is directed to a method and apparatus for automating arm and grasping movement training for rehabilitation of patients with motor impairment. The apparatus includes a wheelchair mounted orthosis having a forearm link and an upper arm link. The '259 and '169 devices utilize fixed springs to compensate for gravity of an arm in order to stabilize the arm at a specific point.

U.S. Pat. Nos. 8,409,117, 8,585,620 and 7,396,337 are directed to orthotic devices that utilize electric motors to directly drive a joint. Such devices are bulky, costly and inefficient.

Based on the above, there is seen to be a need in the art for a semi-passive fluidic orthosis system that consumes comparatively small amounts of energy while suiting a variety of applications. There is also a need for a device that stabilizes a user's arm at any point, allowing the device to assist a user in lifting and carrying objects. Further, there is a need for a device that can assist a user with dropping and catching. The present invention combines the advantages of active and passive methods to assist an individual.

The present invention includes variable stiffness devices that stabilize a user's arm at any point for both the arm and a load, and enable the introduction of damping into the system to assist a user with dropping and catching objects. Further, the present invention provides a lighter orthotic device that utilizes less energy compared to DC devices. The semi-passive device of the present invention can be adjusted to set the stiffness, equilibrium point and damping to whatever a user requires. After these parameters are set (actively), the actuators of the system become inert, requiring no power to function. This dramatically reduces the power consumption as compared to motorized assist devices. Also as the spring means (pneumatic spring actuator) and damper means (hydraulic actuator) are set directly and independently, the controllers can be simpler in that they do not require high fidelity models of a user or their intent.

SUMMARY

The present invention is directed to a semi-passive control system framework and method for assistive orthoses. The device of the present invention provides assistance in the form of gravity and weight compensation, as well as load carrying capacity through hydraulic locking. More specifically, gravity compensation through the use of a pneumatic spring provides a significant increase in the range of motion available to a user. The device can be used for a variety of tasks, thereby increasing the mobility and functionality of a user's arm.

The device of the present invention is semi-passive, and extremely efficient, which allows for significantly longer continuous usage. The device locks hydraulically, allowing for zero power consumption during long periods of usage. The exoskeleton device is lightweight, simplifying everyday wear, and reducing user fatigue common in other systems. The invention also is simple to don and doff, significantly increasing viability for patients with impaired mobility.

In an aspect of the invention, a semi-passive control system includes a pneumatic spring actuator having a shaft, a pressure regulator in communication with the pneumatic spring actuator, a hydraulic locking actuator having a shaft, a hydraulic valve in communication with the hydraulic locking actuator, a pulley wheel, and a cable having a first end in contact with the pulley wheel, first and second side portions extending from opposing sides of the pulley wheel, and a second end adapted to connect to an orthosis device. The system also includes at least one cable clamp attached to the second side portion of the cable and interconnecting the cable to the shaft of the pneumatic spring actuator and to the shaft of the hydraulic locking actuator, and a power source. A central control unit is also provided, including a processor and a computer readable storage medium having program instructions to adjust stiffness, damping or stiffness and damping parameters stored thereon for execution by the central control unit.

In another aspect of the invention, a computer-implemented method for controlling an orthosis joint comprises the steps of receiving, by a computing device, sensor information indicating that a user's limb is moving; determining, by the computing device, that the user's limb is moving in a manner that corresponds with a predefined movement based on the sensor information; determining, by the computing device, parameters associated with the predefined movement; determining, by the computing device, if the parameters require a change in stiffness of an orthosis joint; and determining, by the computing device, if the parameters require a change in damping of the orthosis joint. Upon determining, by the computing device, that the parameters require a change to the stiffness, damping or stiffness and damping of the orthosis joint, the method further comprises activating a power supply to power an adjustment of one or both of a pneumatic spring actuator and a hydraulic actuator, and adjusting, by the computing device, one or both of the pneumatic spring actuator and the hydraulic actuator to achieve the parameters.

Additional objects, features and advantages of the present invention will become more readily apparent from the following detailed description of a preferred embodiment when taken in conjunction with the drawings wherein like reference numerals refer to corresponding parts in the several views.

BRIEF DESCRIPTION OF THE DRAWINGS

The present invention is described in the detailed description which follows, in reference to the noted plurality of drawings by way of non-limiting examples of exemplary embodiments of the present invention.

FIG. 5 shows a cross-sectional view of a pneumatic spring actuator of the present invention;

FIG. 6 shows a cross-sectional view of a hydraulic actuator of the present invention;

DETAILED DESCRIPTION

The present invention relates generally to semi-passive assistive devices for the upper limbs. The present invention may be a system, a method, and/or a computer program product. The computer program product may include a computer readable storage medium (or media) having computer readable program instructions thereon for causing a processor to carry out aspects of the present invention.

Figure 1:
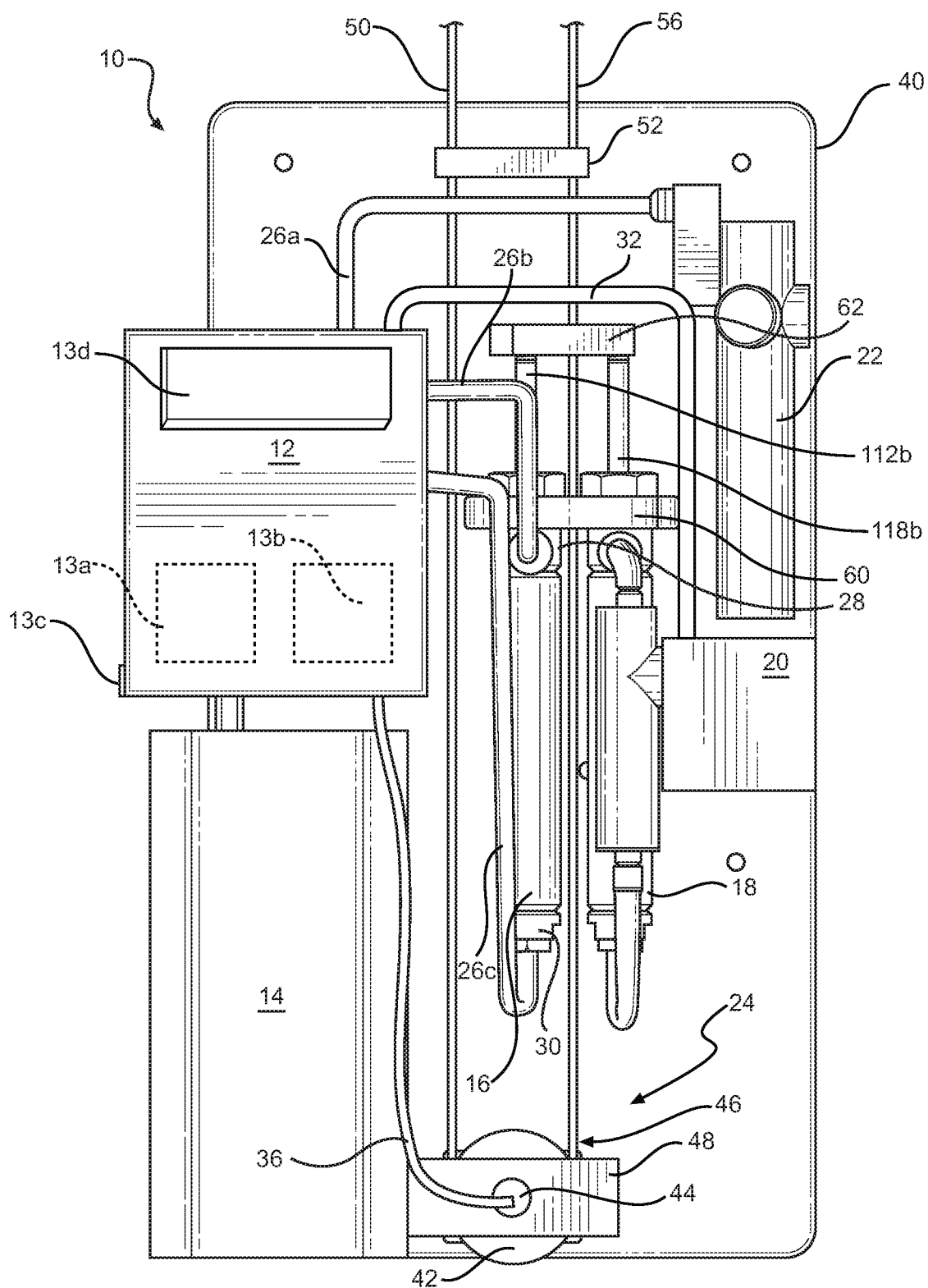
FIG. 1 is a front view of a semi-passive control system of the present invention.

FIG. 1 depicts a semi-passive control system 10 of the present invention for use with assistive orthosis devices. Control system 10 includes a central control unit (computing device) 12, a power supply 14, a pneumatic spring actuator (pneumatic cylinder) 16, a hydraulic actuator (hydraulic cylinder) 18 including a hydraulic valve system 20, a pressure regulator and supply 22, and a pulley system generally indicated at 24. Central control unit 12 is in communication with a first pneumatic supply line 26a connected to pressure regulator and supply 22, a second pneumatic supply line 26b connected to a first end 28 of pneumatic spring actuator 16, and a third pneumatic supply line 26c connected to a second end 30 of pneumatic spring actuator 16. Central control unit 12 is also in communication with hydraulic valve 20 via a cable 32, and pulley system 24 via a cable 36. Central control unit 12 includes a computer processor 13a capable of implementing a control algorithm (computer readable program instructions). For example, central control unit 12 may be a commercial microcontroller adapted for use with the invention, such as an Intel® Edison Microcontroller. Central control unit 12 may also include other standard microprocessor components such as a computer readable storage medium or memory 13b, and an input/output (I/O) interface 13c. A display 13d may also be connected to central control unit 12.

The computer readable storage medium utilized with the present invention is a tangible device that can retain and store instructions for use by an instruction execution device. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. Computer readable program instructions described herein can be downloaded to central control unit 12 from a computer readable storage medium or to an external computer or external storage device via a network, for example, the Internet, a local area network, a wide area network and/or a wireless network. The computer readable program instructions may execute entirely on central control unit 12, partly on central control unit 12, as a stand-alone software package, partly on central control unit 12 and partly on a remote computer or entirely on the remote computer or server (not shown). In the latter scenario, the remote computer may be connected to central control unit 12 through any type of network, including a local area network (LAN) or a wide area network (WAN), or the connection may be made to an external computer (for example, through the Internet using an Internet Service Provider).

In embodiments, semi-passive control system 10 is mounted on a support panel 40, which may be configured as a wearable support as will be discussed in more detail below. Pulley system 24 comprises an idle pulley wheel 42 with a rotary encoder 44 attached thereto, and a cable 46. Rotary encoder 44 is in communication with central control unit 12 via cable 36 and can be any standard rotary encoder for determining the position of pulley wheel 42. For example, rotary encoder can be a MA3 Miniature Absolute Magnetic Shaft Encoder from US Digital. A bearing holder 48 secures pulley wheel 42 and rotary encoder 44 to support panel 40. A first side portion 50 of cable 46 extends through a first aperture (not shown) in a cable guide 52 secured to an upper portion 54 of support panel 40. Likewise, a second side portion 56 of cable 46 extends through a second aperture (not shown) in cable guide 52. A piston mount 60 is utilized to connect pneumatic spring actuator 16 and hydraulic actuator 18 to support panel 40. Additionally, second side portion 56 of cable 46 is fixed to at least one cable clamp 62 mounted to shafts 112b and 118b of respective actuators 16 and 18.

Figure 2:
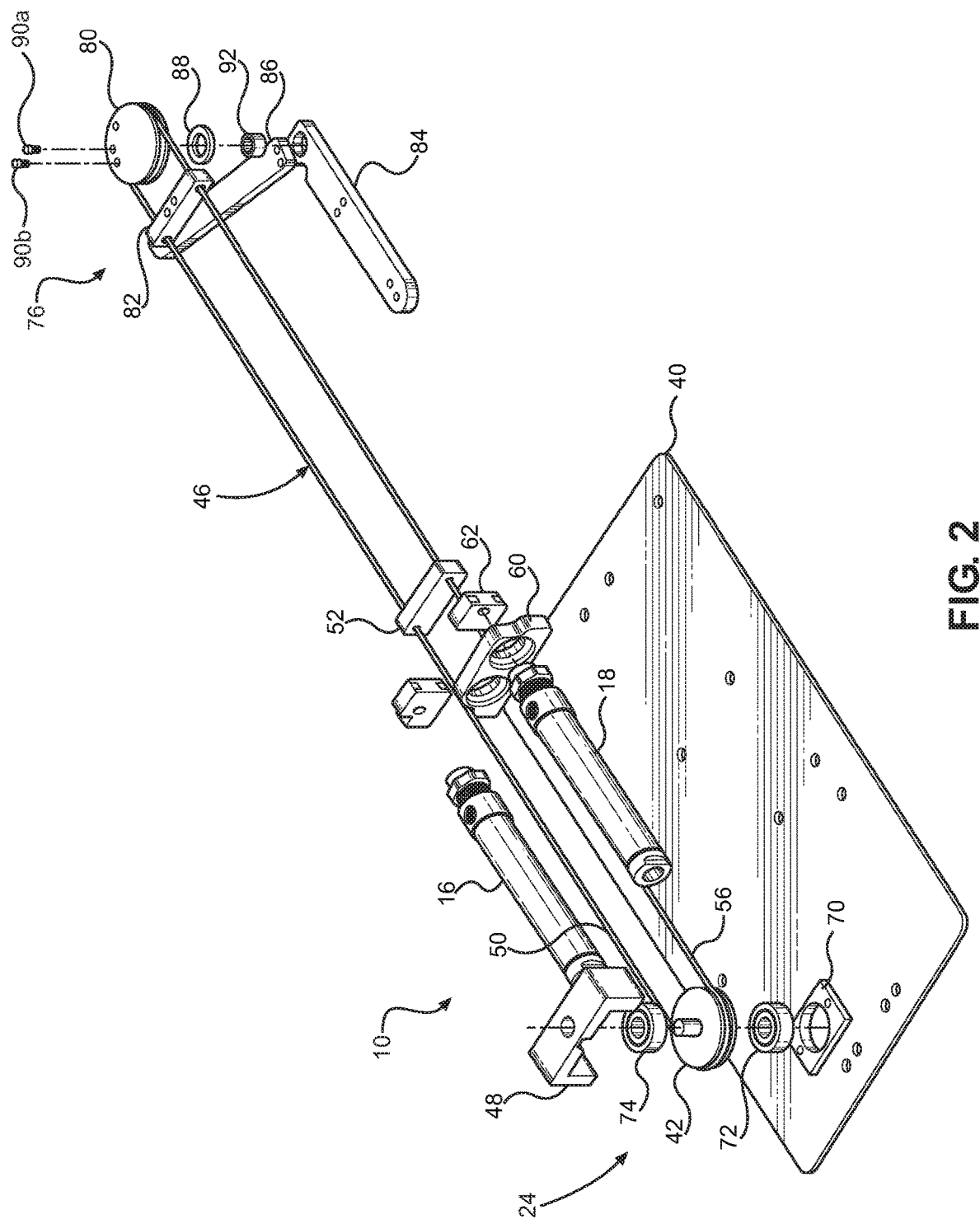
FIG. 2 is a partial exploded view of a semi-passive control system of the present invention connected to an upper arm orthosis device.

Additional details of pulley system 24 will now be discussed with reference to FIG. 2. A bearing holder 70 is connected to support panel 40 for holding a lower bearing 72. Pulley wheel 42 engages lower bearing 72 and an upper bearing 74. Bearing holder 48 engages upper bearing 74 and secures pulley wheel 42, lower bearing 72 and upper bearing 74 to support panel 40. As depicted in FIG. 2, cable clamp 62 may be in the form of first and second cable blocks. It should be understood that semi-passive control system 10 may be utilized with a number of different orthosis devices.

Figure 3:
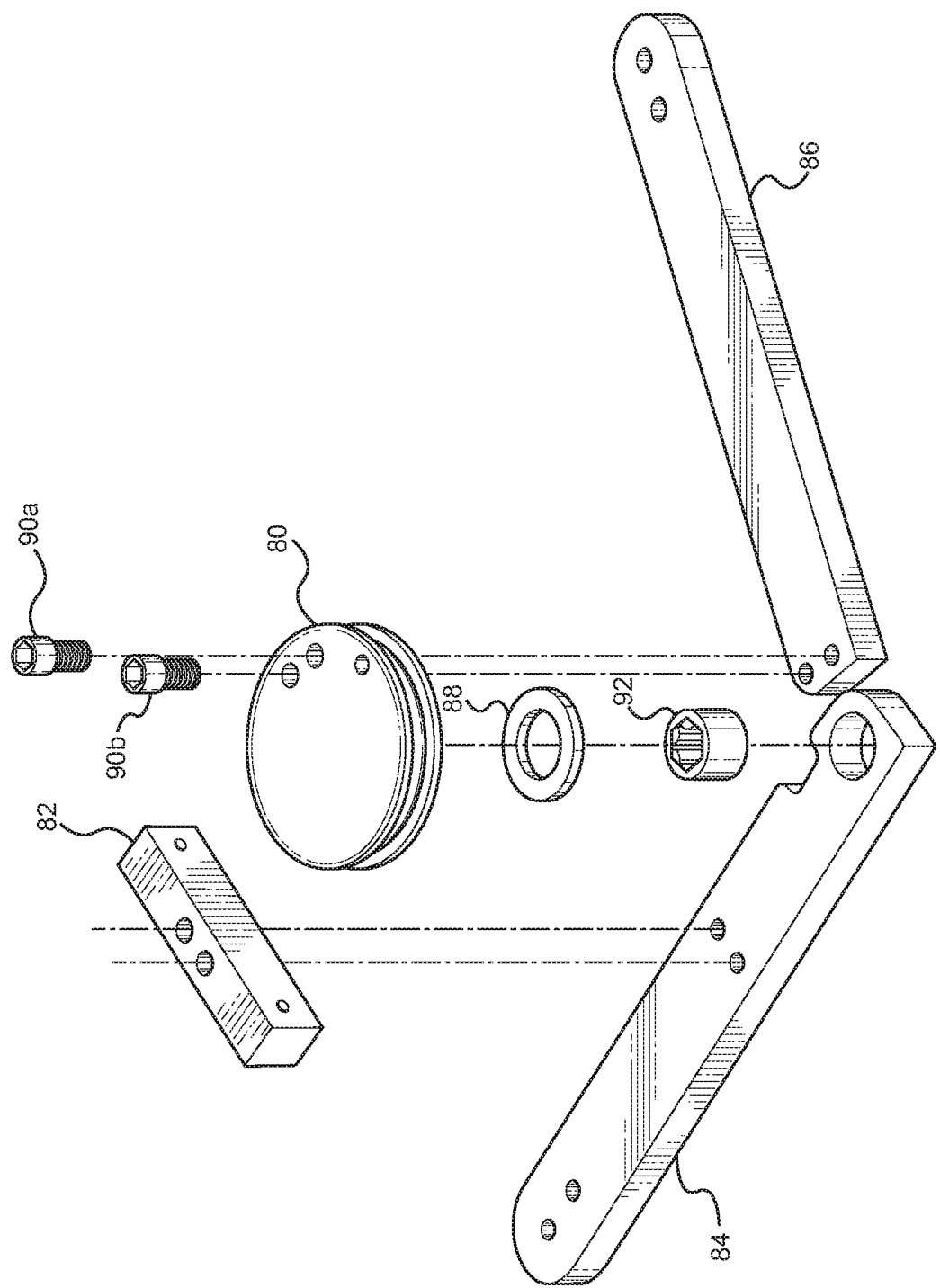
FIG. 3 depicts details of the upper arm orthosis device of FIG. 2.

By way of example, FIG. 2 depicts semi-passive control system 10 in use with an upper arm orthosis device 76. Upper arm orthosis device 76 includes an arm-mounted portion having an elbow pulley 80, a cable guide 82, a bicep mounting bar 84, a forearm mounting bar 86, a spacer 88, a pair of cable clamps 90*a*, 90*b* and a needle roller bearing 92. As depicted in FIG. 3, cable guide 82 is adapted to connect to bicep mounting bar 84 via fasteners (now shown). In use, a first end of cable 32 is connected to pulley wheel 42 and a second end is connected to elbow pulley 80. With this configuration, actuators 16 and 18 are connected through cable 32 to elbow pulley 80 and can be utilized to adjust stiffness and damping effects of elbow pulley 80.

Figure 4:
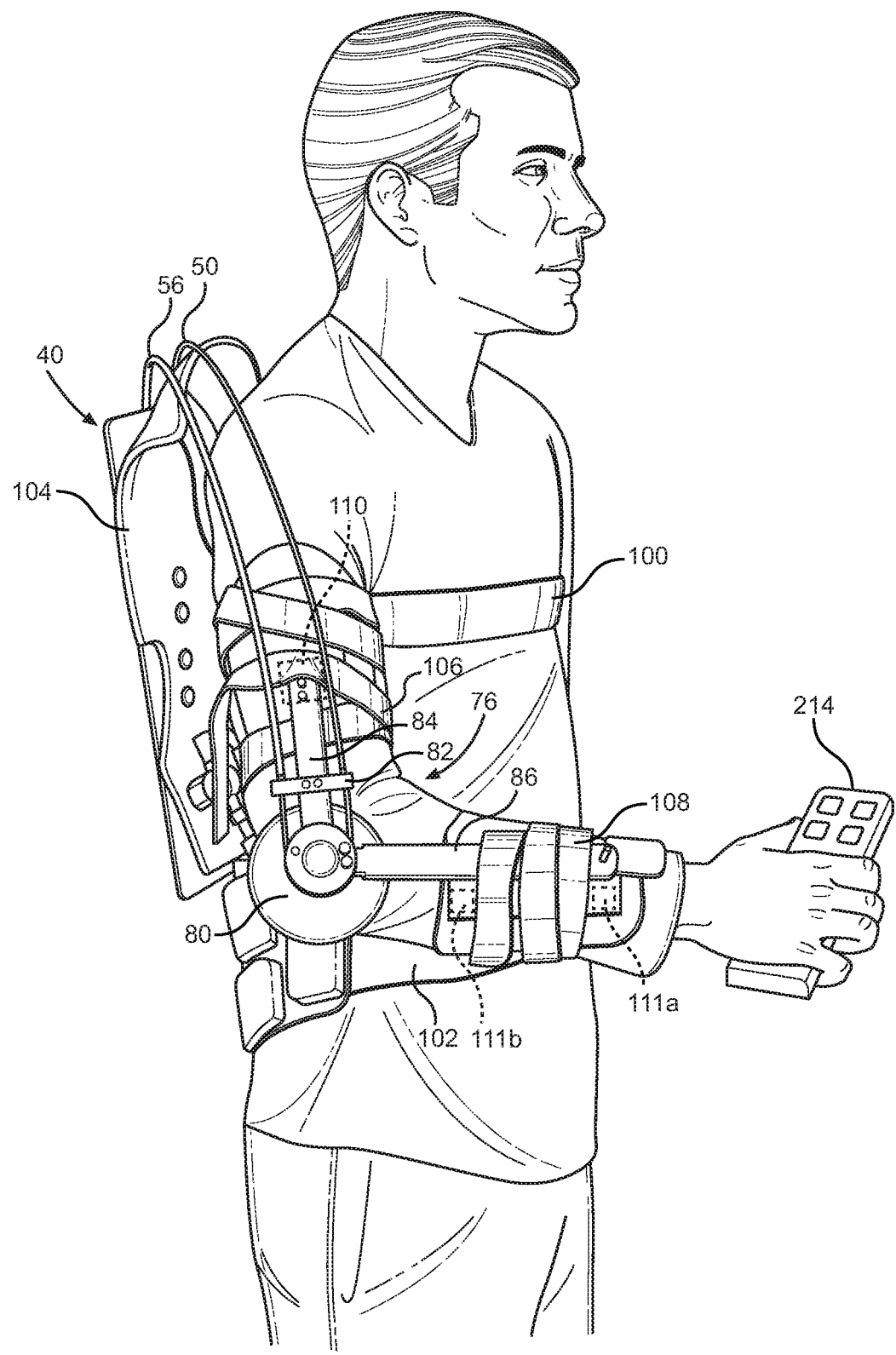
FIG. 4 is a perspective side view of a user wearing an upper arm orthosis device in accordance with embodiments of the invention.

FIG. 4 will now be referenced with respect to additional details of upper arm orthosis device 76. Support panel 40 may be utilized to support components of system 10 near a user, such as on a wheelchair or the like (not shown), or on a user. In embodiments, semi-passive control system 10 is mounted to a user via support panel 40. More specifically, support panel 40 may attached to a user via a means for connecting support panel 40 to a user, such as a chest strap 100 and a waist strap 102. A molded cushion 104 or other suitable structure may be added to a back of support panel 40 to provide comfort to a user. Bicep mounting bar 84 is secured to a user's bicep, such as through straps 106. Likewise, forearm mounting bar 86 is secured to a user's forearm, such as through straps 108. Sensor arrays 110, 111*a*, 111*b*, including a plurality of sensors are positioned on upper arm orthosis device 76 and are adapted to sense signals generated by a user of the device and provide information to central control unit 12. Sensor arrays 110, 111*a*, 111*b* may be comprised of pressure sensors, motion sensors, muscle sensors (e.g. surface electromyography sensors), or other sensors adapted to provide information regarding the user's movements to central control unit 12.

FIG. 5 will now be referenced with respect to details of pneumatic spring actuator 16. Pneumatic spring actuator 16 utilizes a compressible working fluid, such as air or carbon dioxide, to vary both its free length and its stiffness. This is achieved by modulating the pressure of the working fluid in first and second chambers 108, 109 of a piston/cylinder system. Modulation is achieved using high frequency valves. A piston head 112*a* is connected to a piston stem 112*b*. As pressure increases or decreases in either side of piston head 112*a*, the free length of piston stem 112*b* and its stiffness changes. The free length of piston stem 112*b* and stiffness of pneumatic spring actuator 16 may be controlled dynamically or held static, depending on the desired behavior of the overall assistive device. It should be understood that pneumatic cylinder 16 may be commercially available cylinder adapted for use with the present invention. For example, pneumatic cylinder 16 may be an SR-043-D air cylinder from BIMBA®.

FIG. 6 will now be referenced with respect to additional details of hydraulic actuator 18. Hydraulic actuator 18 utilizes an incompressible working fluid, such as water or oil, to vary the damping coefficient. First and second chambers 114, 115 of a piston/cylinder system are connected (as shown in FIG. 1), creating a closed loop of the working fluid. Linear actuation of a piston head 118*a* and piston shaft 118*b* forces fluid to move between the first and second chambers above or below piston head 118*a*. A variable aperture valve 20 (shown in FIG. 7) is connected between first and second chambers 114, 115. By varying the size of the valve aperture, different levels of flow restriction can be achieved. Changing the flow restriction changes the damping coefficient of hydraulic actuator 18. Complete flow restriction results in full locking. The fluidic damping actuator 18 only consumes power when changing the degree of damping. The damping coefficient may be controlled dynamically or held static depending on the desired behavior of the orthosis device used. It should be understood that hydraulic cylinder 18 may be a commercially available cylinder adapted for use with the present invention. For example, hydraulic cylinder 18 may be an SR-043-D from BIMBA®.

Figure 7:
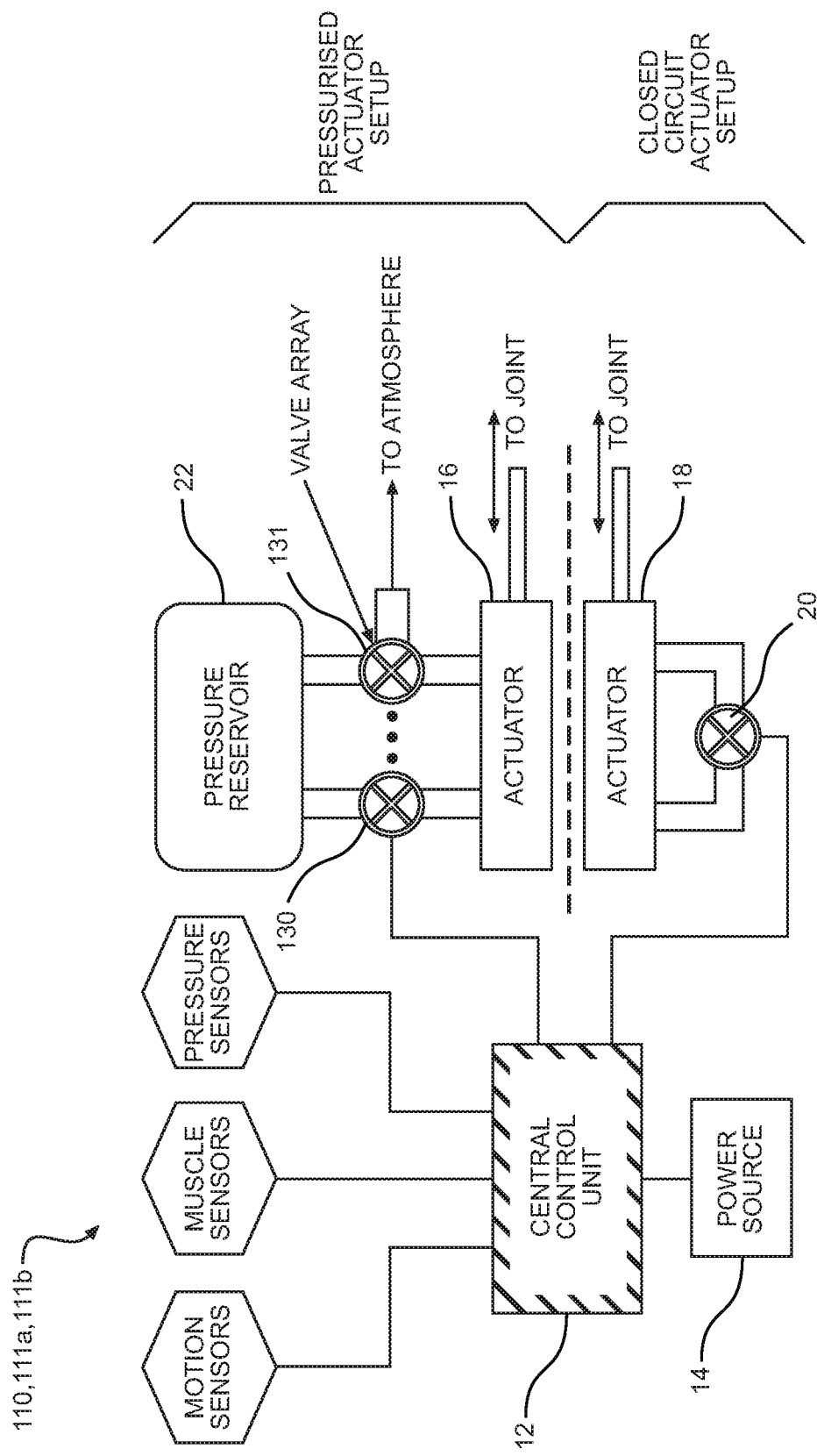
FIG. 7 shows a control schematic of the present invention.

The manner in which semi-passive control system 10 may be operated will now be discussed with reference to FIG. 7. As previously discussed, sensors, such as motion, muscle and pressure sensors, are mounted on upper arm orthosis device 76 and are in communication with central control unit 12. Central control unit 12 utilizes data from sensor arrays 110, 111*a* and 111*b* to control pneumatic spring actuator 16 and hydraulic actuator 18. As depicted, a pressure reservoir or supply 22 in communication with pneumatic spring actuator 16 can be controlled through a valve array, including valves 130, 131. Similarly, hydraulic supply to hydraulic actuator 18 can be controlled through hydraulic valve 20. Central control unit 12 can be programmed to implement a pre-determined series of motions, depending on the data received from the sensor arrays 110, 111*a*, 111*b*. Power supply 14 is also connected to central control unit 12 and respective actuators 16 and 18.

The main benefit of the present invention is that energy is only required to change the dynamic parameters of each joint of an orthotic device. By choosing the optimal parameter set (e.g., stiffness, damping or stiffness and damping setting) for a given set of tasks, and only changing the parameters when necessary, energy expenditure can be greatly reduced. As the dynamic parameters themselves can be changed, it is possible to inject, store and remove energy from the system directly. This allows the energy of a caught object to be absorbed into semi-passive control system 10 either by being dissipated through damping (utilizing the hydraulic actuator 18), or stored so that the energy can be returned in a throw (utilizing the pneumatic spring actuator 16). Similarly, a lifted load can be held by locking the joint (using the hydraulic actuator 18), allowing the weight to be supported by the assistive device, reducing the load experienced by a wearer of orthosis device 76.

The primary features of the semi-passive control system 10 in combination with orthosis device 76, are the pneumatic spring actuator 16 that assists in gravity/load compensation, and the hydraulic actuator 18 that allows users to hold loads without actively powering system 10. Actuators 16 and 18 are the primary source of weight of system 10, and are preferably located on a back of a user, allowing for the majority of the weight of the system 10 to be carried by a user's shoulders/torso, further reducing fatigue. System 10 transmits power from actuators 16 and 18 to a user's elbow joint through cable 46 of orthosis device 76, which drive the elbow to assist in movement of the user. More specifically, the drive system includes a single loop of steel cable 46 and pulleys 42 and 80. Cable brackets or guides 52 and 82 ensure the correct positioning of cable 46. Because of this loop and back plate system, actuators 16 and 18 can be easily added, further simplifying manufacturing and repair.

Figure 8:
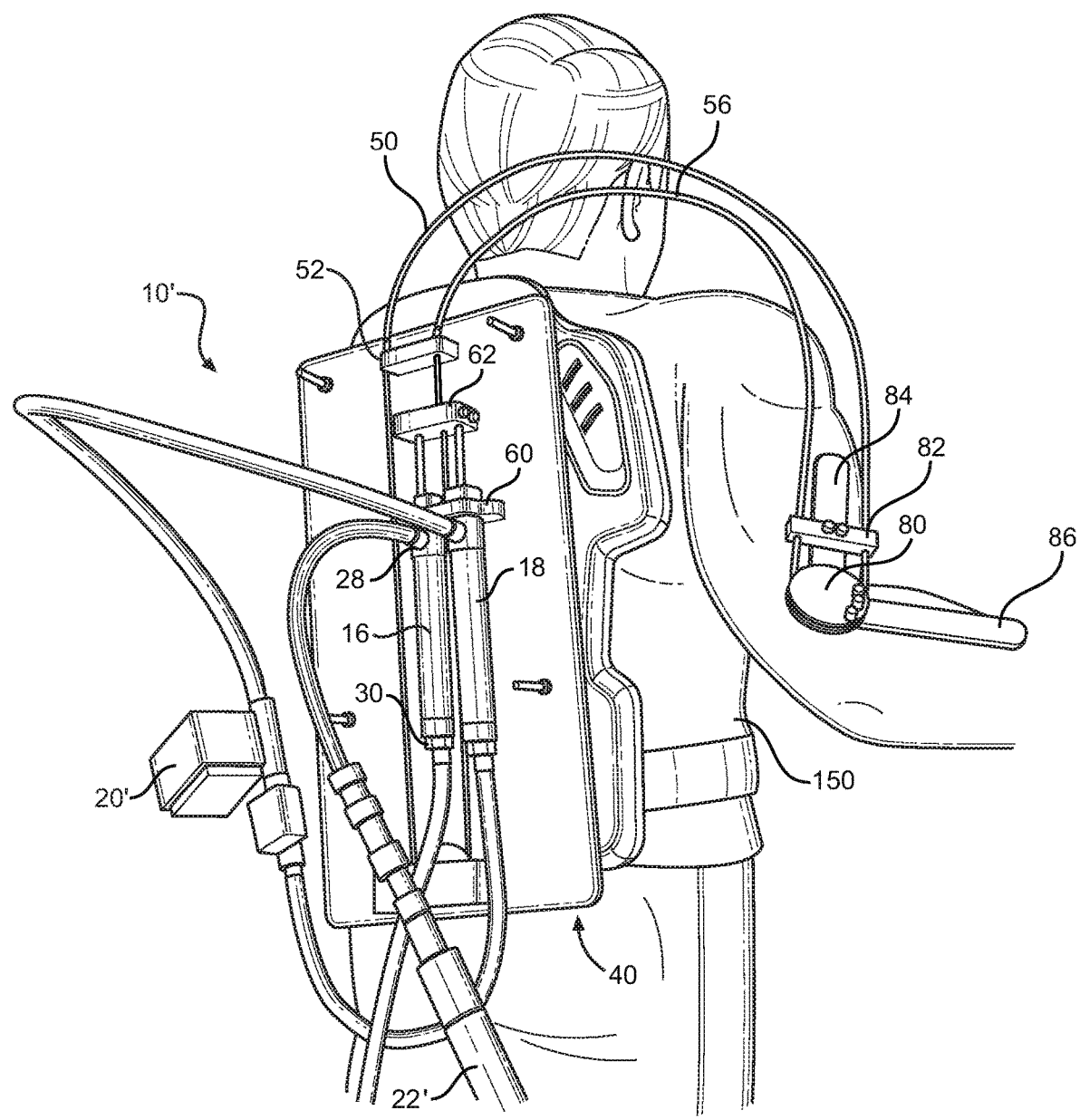
FIG. 8 is a back perspective view of an alternative upper arm orthosis device for use with the present invention.

FIG. 8 depicts an alternative embodiment of the present invention, wherein means for connecting support panel 40 of a semi-passive control system 10' to a user is in the form of a suit 150. More specifically, a support panel 40 with a semi-passive control system 10' mounted thereto may be attached to an upper body suit 150. With this configuration, the weight of semi-passive control system 10' can be distributed to a user's torso through suit 150. It should be understood that semi-passive control system 10' includes the same components as semi-passive control system 10, although some components are not depicted in this figure (e.g. central control unit 12 and power supply 14). Further, some components are shown in a different configuration, such as pressure regulator and supply 22' and hydraulic valve 20'. It should be understood that components of systems 10 and 10' shown may be arranged in different configurations without compromising the function of the invention.

Figure 9:
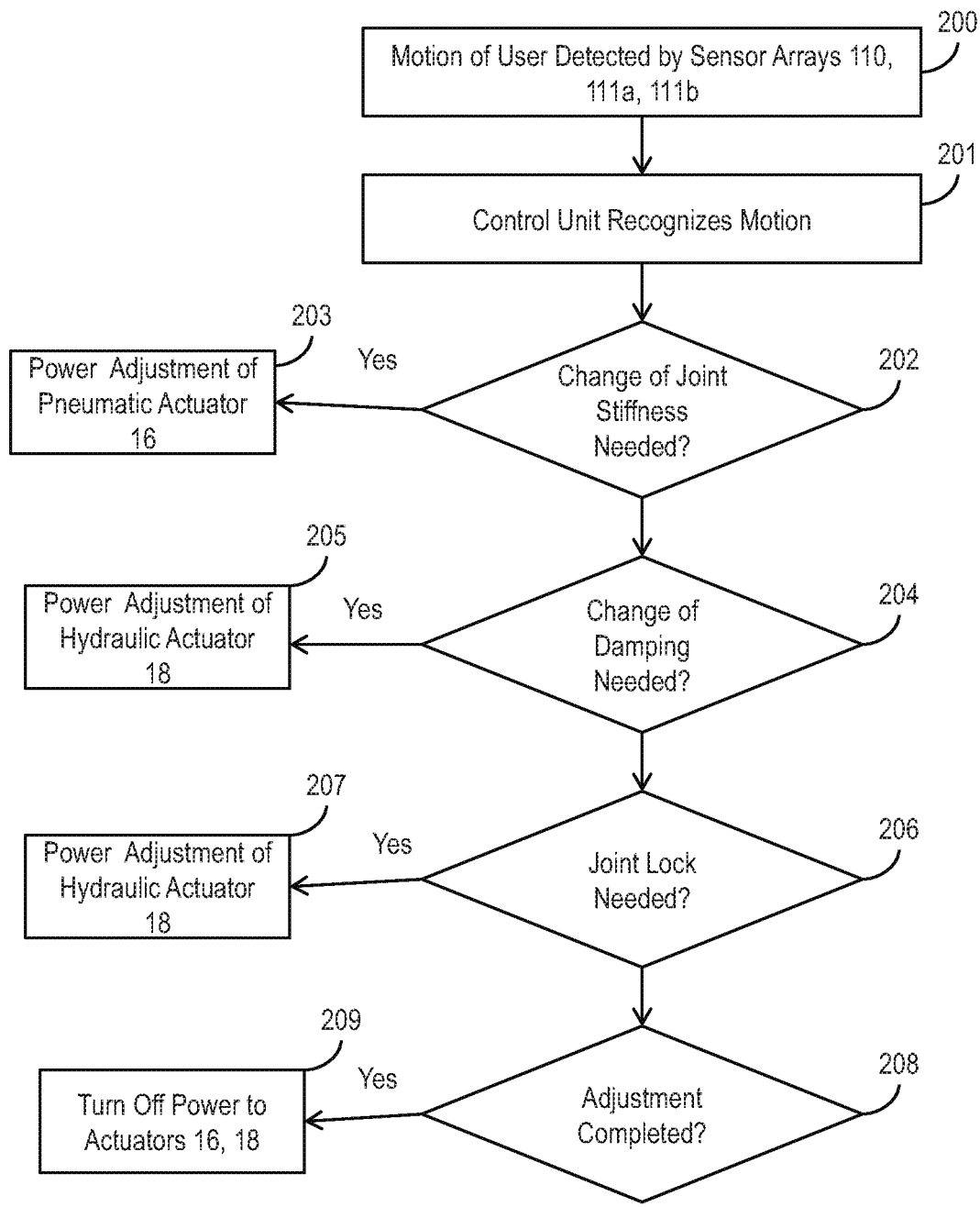
FIG. 9 is a diagram depicting methods of the present invention.

Method of using the present invention will now be discussed with reference to FIG. 9. At step 200 one or more sensors of sensor arrays 110, 111a, 111b detect a motion of a user's arm and send data to central control unit 12. Central control unit 12 then compares the data to information in its memory 13b to determine whether the motion detected is one of a plurality of preprogrammed or predetermined recognized motions or movements at step 201. Once central control unit 12 determines that the movement is a predetermined recognized movement, central control unit 12 utilizes information stored in memory 13b to determine whether the movement requires particular parameters to be set for actuators 16 and 18. More specifically, central control unit 12 looks up desired parameters for a particular motion stored in a look-up table in memory 13b and compares the parameters to the current parameters for actuators 16 and 18. If central control unit 12 determines that an adjustment to actuator 16 and/or 18 is required at steps 202 and/or 204, power supply 14 is actuated to power an adjustment of actuator 16 and/or 18 at steps 203 and/or 205. More specifically, if central control unit 12 determines that a change in joint stiffness is needed at step 202, power supply 14 is actuated to provide an adjustment to pneumatic spring actuator 16 to adjust the position of piston head 112a within actuator 16 at step 203. If central control unit determines that a change in damping is needed at step 204, then power supply 14 is actuated at step 205 to provide power to hydraulic valve 20 to adjust the flow of fluid in hydraulic actuator 18. If central control unit 12 determines that a joint lock is needed (e.g., elbow pulley 80 is locked so that it cannot move) at step 206, then power supply 14 is actuated to provide power to adjust hydraulic actuator 18 to lock hydraulic actuator 18 in a fixed position at step 207 so that cable 46 is held stationary. Once any necessary actuator adjustments are completed at step 208, power supply 14 is deactivated at step 209. It should be appreciated that, with this configuration, power consumption from power supply 14 is limited, and passive assistance is provided by actuators 16 and 18, in accordance with predetermined parameters.

Additionally, a user may utilize a manually control unit, such as a remote control unit 214 to initiate adjustments of actuators 16 and 18. Manual control unit 214 may include, for example, buttons which are preprogrammed to initiate the adjustment of actuators 16 and/or 18 based on predetermined parameters associated with a particular motion. For example, an oft-repeated motion, such a carrying a box, may be associated with a particular button on manual control unit 214, enabling a user to select the button when performing the repetitive motion. In accordance with the present invention, pneumatic actuator 16 can be utilized alone to provide a predetermined joint stiffness, hydraulic actuator 18 can be utilized alone to provide a predetermined damping, or actuators 16 and 18 can be utilized together to provide a combination of desired joint stiffness and damping. Examples of motions that could be aided by the semi-passive control system 10 of the present invention are set forth below.

Example 1: Catching

In a first example, a user is wearing upper orthosis device 76 connected to semi-passive control system 10. In this first example, a user is standing with their arm bent at the elbow in front of them. A mass is dropped onto their hand. This sudden load is detected using sensor arrays 110, 111a, 111b, and the sensor data is conveyed to central control unit 12. Central control unit 12 determines that the movement indicated by the data is a catching movement, which requires a particular preprogrammed damping parameter. Accordingly, central control unit 12 adjusts hydraulic actuator 18 such that damping at the elbow of the user is increased dramatically to the preprogrammed damping parameter, thereby reducing the braking force the individual's elbow needs to apply and minimizing the overextension of the user's elbow joint.

Example 2: Holding

In a second example, a user is wearing upper orthosis device 76 connected to semi-passive control system 10. The user needs to carry a heavy load. By increasing the damping at the elbow joint to full via adjustment of the hydraulic actuator 18, the elbow joint effectively locks in place. This makes orthosis device 76 load bearing, reducing the load experienced by the user. On prior art active devices this would require power for the entire length of time the object is held. However the semi-powered control system 10 of the present invention only requires power to increase the damping at the joint, after which the device can power off.

Example 3: Catch and Throw

In a third example, a user is wearing upper orthosis device 76 connected to semi-passive control system 10. In this example, the user needs to catch an object, and then throw it. Instead of using the damper function of hydraulic actuator 18 to remove the energy from the caught object (as in case 1), pneumatic spring actuator 16 is utilized to absorb the energy. More specifically, when the object is caught, the compressible fluid within pneumatic spring actuator 16 becomes pressurized and cavitates on opposite sides of the actuator 16. Valve array 130, 131 closes, thereby locking pneumatic spring actuator 16 and storing this energy (energy from the pressurized fluid). When the user needs to return the object, valve 130 opens, allowing the stored elastic energy to be released through actuator 16.

Example 4: Reaching

In this example, semi-passive control system 10 is connected to a shoulder orthosis (not shown). The user, an individual with a weakened shoulder, is standing. The equilibrium point of the user's arm remains vertically down and the orthosis device has minimal stiffness or damping. The user wishes to pick up a bowl from head height, and place it in front of them. The user moves their arm upwards. This motion is detected by sensors arrays associated with the orthosis device (not shown), and motion data is relayed to central control unit 12. Central control unit 12 adjusts actuators 16 and/or 18 such that the equilibrium point of the arm is increased and the arm balances at shoulder height. By increasing the stiffness of the shoulder, it supports the mass of the arm, allowing the user to both reach the bowl and place it on the table. Power is only required during the change in stiffness and equilibrium point. This cannot be achieved by a passive device, and would require a constant power drain from an active device.

Although described with reference to a preferred embodiment of the invention, it should be readily understood that various changes and/or modifications can be made to the invention without departing from the spirit thereof. For instance, the means for attaching the orthosis device to a user can take on any number of known forms, and the support plate could be mounted to a wheelchair, or in front of a user, depending on the particular use of the device and the needs of a user.

What is claimed is:

1. A semi-passive control system comprising:
   a pneumatic spring actuator including a shaft;
   a pressure regulator in communication with the pneumatic spring actuator;
   a hydraulic locking actuator including a shaft;
   a hydraulic valve in communication with the hydraulic locking actuator;
   a pulley wheel;
   a cable having a first end in contact with the pulley wheel, first and second side portions extending from opposing sides of the pulley wheel, and a second end adapted to connect to an orthosis device;
   at least one cable clamp attached to the second side portion of the cable and interconnecting the cable to the shaft of the pneumatic spring actuator and to the shaft of the hydraulic locking actuator;
   a power supply; and
   a central control unit including a processor and a computer readable storage medium having program instructions stored thereon for execution by the central control unit to adjust current parameters including a stiffness parameter, a damping parameter or the stiffness and damping parameters.

2. The system of claim 1, wherein the program instructions include:
   program instructions to receive sensor information from the orthosis device worn by a user;
   program instructions to determine that a user's limb is moving in a manner that corresponds with a predefined movement based on the sensor information;
   program instructions to determine desired parameters associated with the predefined movement;
   program instructions to determine if the desired parameters require a change in stiffness of an orthosis joint;
   program instructions to determine if the desired parameters require a change in damping of the orthosis joint;
   program instructions to actuate the power supply to power the adjustment of the current parameters of one or both of the pneumatic spring actuator and the hydraulic locking actuator upon determining that the desired parameters require the change to the stiffness, damping or stiffness and damping of the orthosis joint;
   program instructions to adjust one or both of the pneumatic spring actuator and the hydraulic locking actuator to achieve the desired parameters.

3. The system of claim 1, wherein the program instructions include program instructions to deactivate the power supply upon completion of the adjusting the one or both of the pneumatic spring actuator and the hydraulic locking actuator to achieve the desired parameters.

4. The system of claim 1, further comprising a support panel, wherein the pneumatic spring actuator, pressure regulator, hydraulic locking actuator, hydraulic valve, pulley wheel, power supply and central control unit are mounted to the support panel.

5. The system of claim 4, further comprising a for attaching the support panel to a user.

6. The system of claim 1, further including the orthosis device comprising:
   an elbow pulley, wherein the second end of the cable extends about the elbow pulley;
   a forearm mounting bar;
   a bicep mounting bar pivotally connected to the forearm mounting bar;
   at least one sensor array; and
   a cable guide mounted to the bicep mounting bar and connecting the cable to the bicep mounting bar;
   wherein the stiffness parameter of the pneumatic spring actuator, the damping parameter of the hydraulic locking actuator, or a combination of the stiffness parameter of the pneumatic spring actuator and the damping parameter of the hydraulic locking actuator is transmitted to the elbow pulley through the cable.

7. The system of claim 1, further comprising a manual control device for activating a predefined set of stiffness, damping or stiffness and damping parameters.

8. A computer-implemented method for controlling an orthosis joint utilizing a semi-passive control system including:
   providing the semi-passive control system, the semi-passive control system including:
   a pneumatic spring actuator including a shaft;
   a pressure regulator in communication with the pneumatic spring actuator;
   a hydraulic locking actuator including a shaft;
   a hydraulic valve in communication with the hydraulic locking actuator;
   a pulley wheel;
   a cable having a first end in contact with the pulley wheel, first and second side portions extending from opposing sides of the pulley wheel, and a second end adapted to connect to an orthosis device;
   at least one cable clamp attached to the second side portion of the cable and interconnecting the cable to the shaft of the pneumatic spring actuator and to the shaft of the hydraulic locking actuator;
   a power supply; and
   a central control unit including a processor and a computer readable storage medium having program instructions stored thereon for execution by the central control unit to adjust current parameters including a stiffness parameter, a damping parameter or the stiffness and damping parameters;
   receiving, by the central control unit, sensor information indicating that a user's limb is moving;
   determining, by the central control unit, that the user's limb is moving in a manner that corresponds with a predefined movement based on the sensor information;
   determining, by the central control unit, desired parameters associated with the predefined movement;
   determining, by the central control unit, if the desired parameters require a change in stiffness of an orthosis joint;
   determining, by the central control unit, if the desired parameters require a change in damping of the orthosis joint;
   upon determining, by the central control unit, that the desired parameters require a change to the stiffness parameter, the damping parameter or the stiffness and damping parameters of the orthosis joint, activating a power supply to power an adjustment of one or both of the pneumatic spring actuator and the hydraulic locking actuator; and adjusting, by the central control unit, one or both of the pneumatic spring actuator and the hydraulic locking actuator to achieve the desired parameters.

9. The computer-implemented method of claim 8, wherein the desired parameters require locking of the joint, and the adjusting comprises adjusting the hydraulic locking actuator to a maximum damping to lock the joint.

10. The computer-implemented method of claim 8, wherein the adjusting comprises adjusting both the hydraulic locking actuator and the pneumatic spring actuator.

11. The computer-implemented method of claim 8, wherein the adjusting comprises adjusting only the pneumatic spring actuator.

12. The computer-implemented method of claim 8, wherein the adjusting comprises adjusting only the hydraulic locking actuator.

13. The computer-implemented method of claim 8, further comprising deactivating the power supply upon completion of the adjusting the one or both of the pneumatic spring actuator and the hydraulic locking actuator to achieve the desired parameters.

14. The computer-implemented method of claim 8, wherein the orthosis device is an upper-arm orthosis device and the sensor information is received from the upper-arm orthosis device.

\* \* \* \* \*